United States Patent [19]

Bennetto et al.

[11] Patent Number: 5,122,456
[45] Date of Patent: * Jun. 16, 1992

[54] AMPEROMETRIC METHOD FOR THE QUANTITATIVE DETERMINATION OF 1,4-DIHYDRONICOTINAMIDE ADENINE DINUCLEOTIDE (NADH) IN SOLUTION

[75] Inventors: Hugh P. Bennetto; Gerard M. Delaney; Jeremy R. Mason; Christopher F. Thurston; John L. Stirling, all of London; David R. DeKeyzer, Needingworth; William H. Mullen, Ely, all of Great Britain

[73] Assignee: Cambridge Life Science plc, Cambridge, United Kingdom

[*] Notice: The portion of the term of this patent subsequent to Nov. 13, 2007 has been disclaimed.

[21] Appl. No.: 295,035
[22] PCT Filed: Apr. 29, 1988
[86] PCT No.: PCT/GB88/00338
§ 371 Date: Feb. 24, 1989
§ 102(e) Date: Feb. 24, 1989
[87] PCT Pub. No.: WO88/08447
PCT Pub. Date: Nov. 3, 1988

[30] Foreign Application Priority Data
May 1, 1987 [GB] United Kingdom ............... 8710472

[51] Int. Cl.$^5$ .................. C12Q 1/32; C12Q 1/00; C12Q 1/54; C12Q 1/26
[52] U.S. Cl. .......................................... 435/76; 435/4; 435/14; 435/25; 435/1.74; 435/176; 435/177; 435/181; 435/288; 435/291; 435/180; 435/817
[58] Field of Search ............... 435/817, 288, 9, 7, 435/4, 25, 26, 14, 174, 291, 176, 177, 180, 181

[56] References Cited

U.S. PATENT DOCUMENTS

| | | | |
|---|---|---|---|
| 4,044,193 | 8/1977 | Petrow et al. | 429/40 |
| 4,166,143 | 8/1979 | Petrow et al. | 427/115 |
| 4,293,396 | 10/1981 | Allen et al. | 204/106 |
| 4,321,123 | 3/1982 | Nakamura et al. | 435/288 |
| 4,376,689 | 3/1983 | Nakamura et al. | 435/288 |
| 4,478,696 | 10/1984 | Allen | 204/105 |
| 4,970,145 | 11/1990 | Bennetto et al. | 435/14 |

FOREIGN PATENT DOCUMENTS

| | | |
|---|---|---|
| 247850 | 5/1987 | European Pat. Off. |
| 54-140594 | 4/1978 | Japan |
| 593439 | 10/1980 | U.S.S.R. ............... 435/817 |

OTHER PUBLICATIONS

Eggers et al (1982) Enzyme Immunoassay with Flow Amperometric Detection of NAD Clin Chem 2819:1848-1851.
Stryer (1981) Biochemistry, Freenan Inc NY p. 308-315.
Gorton, L., et al., 161 J. Electroanalyt Chem. 103-20 (1984).
Kimura, Y., and Nihi, K., 1 Analytical Science 271-4 (1985).
Kalys, J. J., 2 Biosensors 3-13 (1986).
Johnson, D. G. et al., 58 Analyt. Chem. 41R-43R and 48R (1986).
Moiroux, I., and Elving, P. J., 102 J.A.C.S. 6533-6538 (1980).
Cenas et al., Electrocatalytic Oxidation of NADH on Carbon Black Electrodes, J. Electroanal. Chem. 189 (1985) 163-169.

Primary Examiner—Christine Nucker
Assistant Examiner—David R. Preston
Attorney, Agent, or Firm—St. Onge Steward Johnston & Reens

[57] ABSTRACT

A method is disclosed for the quantitative determination of 1,4-dihydronicotinamide adenisne dinucleotide (NADH) in solution. The method comprises contacting the NADH-containing solution with an activated carbon electrode, maintaining the carbon electrode at a controlled, fixed potential effective to cause oxidation of NADH at the electrode surface, and measuring the current output from the carbon electrode, wherein there is used a noble metal containing preferably a platinized or palladized activated carbon electrode comprising a porous, heterogeneous, resin-bonded layer of activated carbon or graphite particles comprising the finely divided noble metal preadsorbed thereon and bonded together with a natural or synthetic resin binder, preferably a hydrophobic resin such as polytetrafluoroethylene.

24 Claims, 7 Drawing Sheets

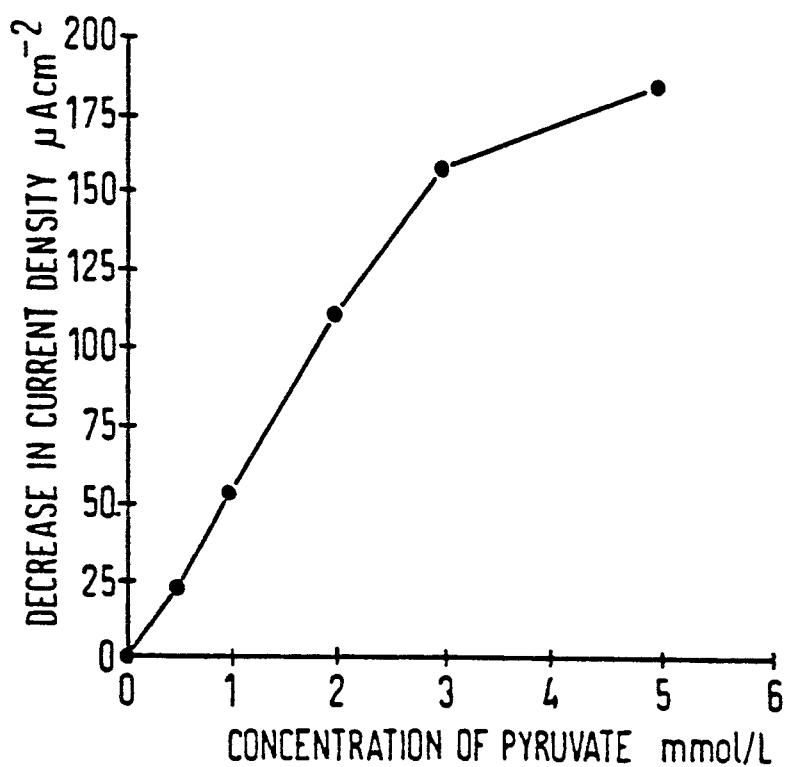
FIG.7
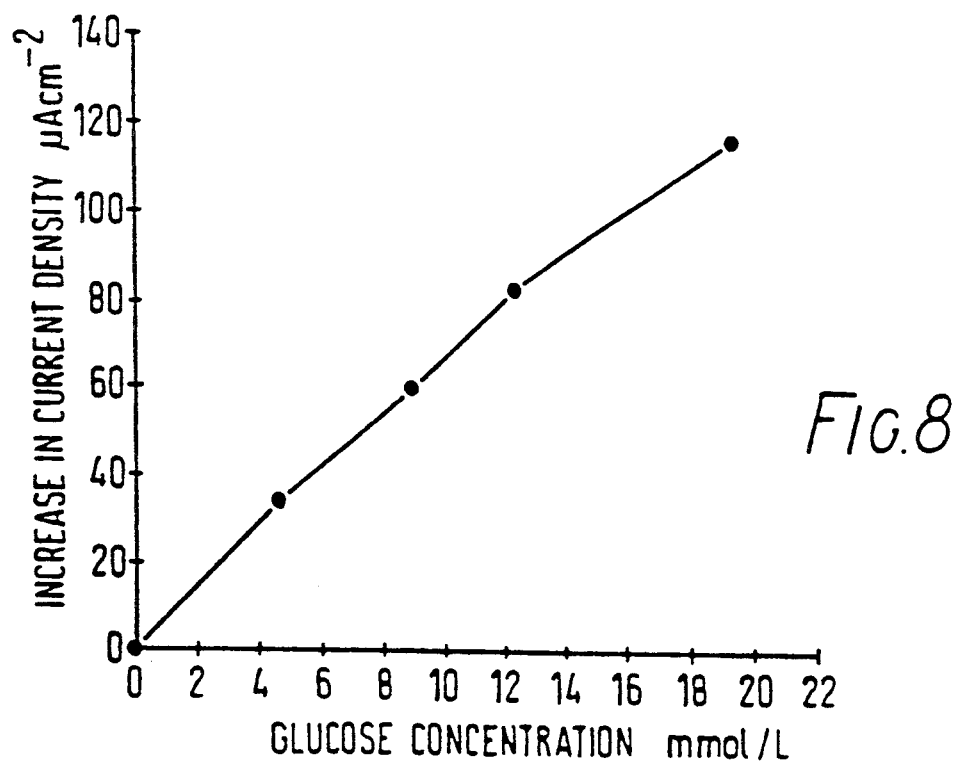
FIG.8
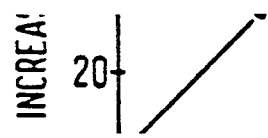

AMPEROMETRIC METHOD FOR THE QUANTITATIVE DETERMINATION OF 1,4-DIHYDRONICOTINAMIDE ADENINE DINUCLEOTIDE (NADH) IN SOLUTION

This invention relates to a method for the quantitative determination of 1,4-dihydronicotinamide adenine dinucleotide (NADH) in solution.

NADH and its oxidised counterpart NAD are cofactors in numerous enzyme catalysed redox reactions. In some, an enzyme substrate is oxidised in the presence of cofactor NAD and a suitable oxidase or dehydrogenase to yield NADH in solution; in others an enzyme substrate is reduced in the presence of cofactor NADH to yield NAD in solution. In many cases, determination of the NADH concentration can be used as an indicator of substrate concentration, or as a means of following the course of an enzyme reaction involving NADH (or NAD).

It is known that NADH concentration in solution can be measured colorimetrically, but colorimetric methods on the whole are disadvantageous. Much more advantageous are electrochemical methods, but attempts to determine NADH electrochemically have so far not met with any very great degree of success. It is known, for example, that NADH concentration can be determined by an amperometric assay in which NADH is oxidised at an electrode at a fixed, controlled, potential, the current passing under suitable conditions being proportional to NADH concentration. Unfortunately the electrochemical oxidation of NADH requires a high overpotential, and the NADH is generally not oxidised cleanly at the electrode surface; for example, in many cases the surface of the electrode is quickly fouled by formation of a surface film which affects the size and speed of the electrochemical response: I. Moiroux and P. J. Elving, J. Amer. Chem. Soc. (1980) 102, 6533-6538, and D. G. Johnson, M. D. Ryan and G. S. Wilson, Analyt. Chem. (1986) 58, 42R.

There have been many attempts to avoid these problems. For example, it has been proposed to use modified electrodes coated with a layer of conducting organic salts: J. J. Kulys, Biosensors (1986) 2, 3-13. Alternatively it has been proposed to use an adsorbed redox mediator such as Meldola's blue to couple the oxidation reaction more effectively to the electrode and/or to lower the oxidation potential: L. Gorton et al., J. Electroanalyt. Chem. (1984), 161, 103-20. In another proposal redox mediators have been used in free solution. For example, methoxy phenazine methosulphate has been used with a modified pyrolitic graphite electrode: Y. Kimura and K. Nihi, Analytical Sciences (1985), 1, 271-4. Other experiments have been carried out with platinum, graphite and glassy carbon electrodes, but as yet no electrochemical method for the determination of NADH has been developed which is both rapid and reproducible.

In accordance with the present invention it has been discovered that NADH can be oxidised cleanly, with good amperometric response, both in buffer solutions containing NADH alone, and in solutions containing enzyme, enzyme substrate and NADH, using an activated carbon electrode of a type used in fuel cell technology and comprising a heterogeneous resin-bonded layer of noble metal containing, preferably platinised or palladised (which terms as used herein include materials containing or treated with platinum and/or palladium oxide, as well as materials containing or treated with platinum or palladium metal) carbon or graphite particles bonded with a natural or synthetic resin binder, preferably a synthetic, hydrophobic binder, such as a fluorocarbon resin, most preferably polytetrafluoroethylene. Preferably a platinised or palladised activated carbon electrode is used in which the carbon or graphite particles are platinised or palladised by adsorbing or depositing colloidal platinum or palladium metal, or platinum or palladium oxide, onto the surface of the powder particles before bonding, the resultant electrode comprising a heterogeneous porous activated carbon powder layer with colloidal platinum or palladium, or the corresponding oxides, distributed substantially uniformly throughout the layer. The resin-bonded layer of platinised or palladised activated carbon or graphite particles may be self-supporting, but will usually be supported by a support member, preferably an electrically conductive support member, and preferably a layer of electrically conductive carbon paper to which the platinised or palladised carbon or graphite particles are bonded as a surface layer, or impregnated into a carbon fibre web. Whilst the platinised and palladised materials are preferred, other noble metal containing activated carbon electrodes, e.g. gold containing electrodes, may be used.

Herein, the terms "platinised" and "palladised" include the oxides unless the context requires otherwise.

Also herein, the terms "activated" carbon, "activated" graphite, etc. refer to highly porous, high surface area carbon and graphite materials having surface areas of 50 m$^2$/g or greater, and more usually in excess of 200 m$^2$/g, e.g. from 200 to 600 m$^2$/g or higher. Such high surface area materials are obtained, for example, by heat treatment of carbon or graphite powders in steam or $CO_2$ to give a high surface area product generally referred to in the art as "activated carbon".

Quite apart from the stability, reproducibility, and rapid response times already mentioned, a further particular advantage of the present materials is that they can be used to monitor NADH concentrations at relatively low potentials, e.g. in the range 0 to 600 mV or even at negative potentials with reference to the standard Ag/AgCl reference electrode, as against the 750 mV and upwards required to monitor NADH concentrations using glassy carbon or graphite electrodes. The present electrodes are thus characterised by relatively low background current, and hence improved sensitivity. The electrodes are also characterised by their low response to potentially interfering species, such as uric acid, frequently present in biological or clinical samples.

The preferred electrode substrates used in accordance with this invention are, in fact, commercially available materials sold by the Prototech Company of Newton Highlands, Mass., and used heretofore as electrocatalytic gas diffusion electrodes in fuel cells. The preparation of such materials is described in detail in U.S. Pat. No. 4,044,193, U.S. Pat. No. 4,166,143, U.S. Pat. No. 4,293,396 and U.S. Pat. No. 4,478,696, to which reference should be made for full details. In broad detail, however, colloidal platinum with a particle size in the range 15 to 25 Angstroms (1.5 to 2.5 nm) is adsorbed onto the surface of powdered carbon (particle size 50 to 300 Angstroms:5 to 30 nm), for example, by formation of a platinum sol in situ in the presence of powdered carbon which acts as a nucleating agent for the sol. The platinised carbon particles are then moulded onto an electrically conductive supporting structure, e.g. electrically conductive carbon paper, using a synthetic resin binder, preferably a fluorinated hydrocarbon resin, and especially polytetrafluoroethylene. Alternatively, platinum or palladium oxide having a similar particle size range may be used in place of the colloidal platinum, and adsorbed onto the carbon or graphite particles in a similar manner.

In an alternative, disclosed in U.S. Pat. No. 4,293,396, the platinised carbon particles are impregnated into a preformed porous carbon cloth and bonded therein using the fluorocarbon resin, preferably polytetrafluoroethylene. It is to be understood, however that the present invention is not limited to the use of Prototech materials, but embraces other similar substrate materials comprising a porous resin-bonded layer of platinised or palladised, or other noble metal containing activated carbon or graphite particles.

Whilst the preferred resin binders used to bind the platinised or palladised carbon or graphite particles are hydrophobic fluorocarbon resins, particularly polytetrafluoroethylene, other suitable natural or synthetic resin binders may be used, for example polyethylmethacrylate, polyvinyl acetate, polyvinyl chloride, polycarbonates, poly(4-methylpentene-1) polyisoprene, isoprene, polychloroprene, poly(1,3-butadiene), silicone rubber and gelatin.

The proportion of binder to the noble metal containing activated carbon or graphite particles, on a weight basis, may range from 10 to 75% binder and 90 to 25% activated carbon or graphite, preferably 20 to 50% binder and, correspondingly, 80 to 50% activated carbon or graphite. The loading of noble metal, e.g. platinum or palladium or their corresponding oxides, or gold, on the activated carbon or graphite particles may range from 1 to 10% based on the total weight of activated carbon or graphite and binder, preferably from 2 to 8%, most preferably from 4 to 6%.

Instead of moulding the resin/activated platinised or palladised carbon powder directly onto the surface of a suitable support, e.g. directly onto the surface of electrically conductive carbon paper, the mixture of binder and platinised or palladised carbon powder may be suspended in a suitable inert medium, and applied to the surface of the substrate by a screen printing technique, thereby providing a thin film of resin-bonded platinised or palladised carbon particles on the surface of the substrate.

As well as the direct quantitative measurement of NADH in solution, the electrodes and process of the present invention may be used in the quantitative determination of NADH generated or consumed in situ for example by the enzymatic reaction between an enzyme and its cofactor. Such reactions include for example the conversion of pyruvate to lactate by lactate dehydrogenase, i.e. the reaction

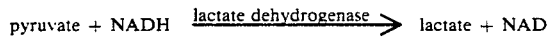

pyruvate + NADH $\xrightarrow{\text{lactate dehydrogenase}}$ lactate + NAD which reaction may be monitored by the decrease in NADH concentration; and the oxidation of glucose to gluconolactone by the reaction

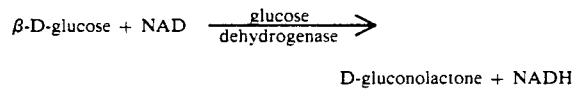

$\beta$-D-glucose + NAD $\xrightarrow{\text{glucose dehydrogenase}}$ D-gluconolactone + NADH which can be monitored by the increase in NADH concentration as the reaction proceeds. To this end the activated platinised or palladised carbon electrodes used in accordance with this invention may have an enzyme such as lactate dehydrogenase or glucose dehydrogenase incorporated into or immobilised onto the resin-bonded carbon layer by any of the enzyme immobilization techniques known in the art and taught for example in EP-A-0 247 850.

In a further modification of this concept the present invention also envisages a one off, disposable enzyme electrode and method in which the enzyme electrode itself comprises not only the immobilised enzyme, but also the appropriate cofactor for that enzyme, either NAD or NADH as the case may be, the enzyme electrode thus having the capability of responding amperometrically to the activity of the enzyme, as determined by the change in NADH concentration, when in contact with a sample, e.g. a clinical or biological sample, containing the relevant substrate for that enzyme, irrespective of whether that sample contains the necessary cofactor, since that is supplied by the electrode itself. The NAD or NADH cofactor may be incorporated into the electrode in any suitable manner such as impregnation with a suitable solution of either NAD or NADH and drying.

As is also well known in the art, the surface of the electrode material may or may not be protected by a porous membrane, such as a polycarbonate film having a pore size of for example about 0.03 $\mu$m. Other suitable membrane materials may also be used.

The invention is further described with reference to the accompanying drawings, in which:

FIG. 7 shows the results of another experiment involving the response of the electrode to pyruvic acid;

FIG. 8 shows the response of the electrode to NADH produced in situ by the enzymatic oxidation of glucose using glucose dehydrogenase;

Figure 1:
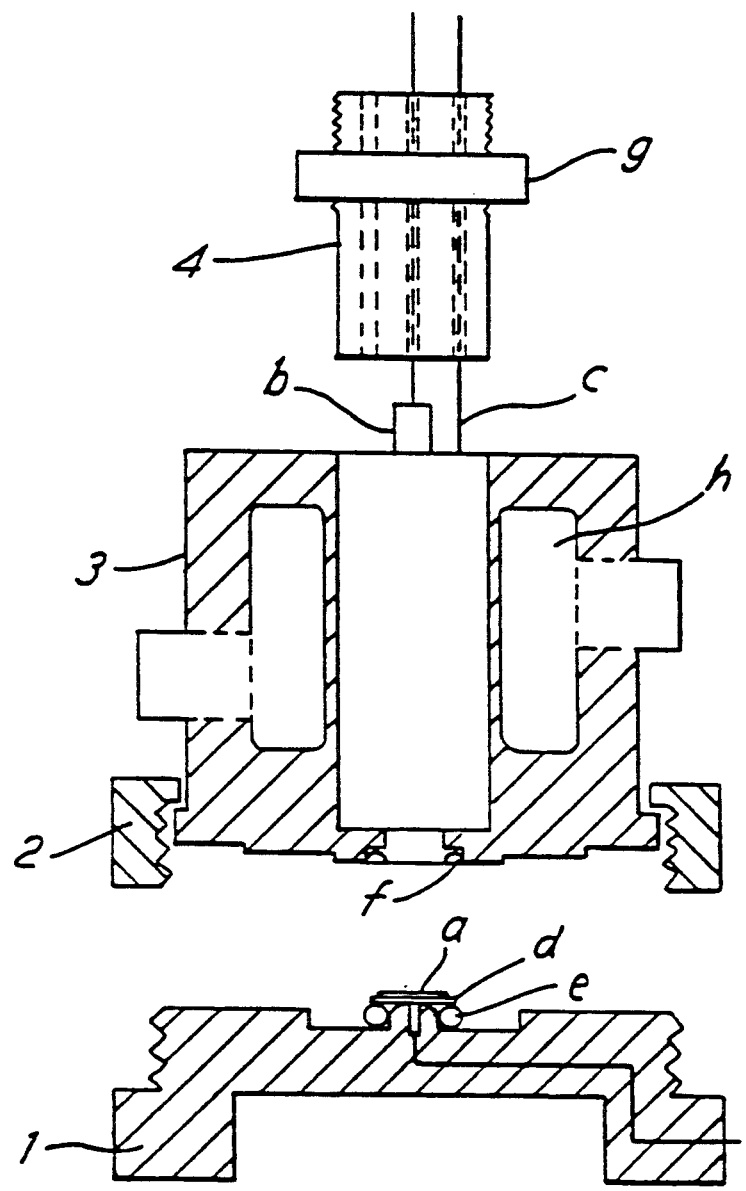
FIG. 1 is a diagrammatic section through a modified Rank Brothers electrochemical cell used to test the NADH response of the activated carbon electrodes in accordance with this invention.

In the following Examples, various platinised or palladised carbon paper (PCP) electrodes were tested for their response to NADH in a modified Rank oxygen electrode system (Rank Brothers, Bottisham, Cambridge) and as shown in the accompanying drawings (FIG. 1). The modified Rank cell system comprises a two-part cell having a base (1) and an annular jacket (2)

enclosing a water chamber (h), through which water may be circulated to control the temperature of the cell, the two parts being connected together by the captive threaded collar (3). Centrally located in the base (1) is a platinum contact button (d) onto which is placed the test disc (a) of paper electrode material and which is held in place on the platinum contact by rubber O-ring seals (e) and (f) when the two parts of the cell are coupled together.

Inserted into the top of the cell, which of course will contain the test NADH-containing solution, is a stopper (4) supported by an adjustable collar (g) and in which are mounted a platinum counter electrode (b) and an Ag/AgCl reference electrode (c). The tests were carried out with the working electrode poised at various potentials in the range 100 to 600 mV with reference to the Ag/AgCl electrode. Other tests were carried out in a two electrode cell as illustrated in FIG. 16 of EP-A-0 247 850 and as described therein in detail. In the two electrode cell embodiment, the electrode material is held against a platinum contact button in the base of the cell by means of a polycarbonate (0.03 μm pore size) membrane and to which the NADH containing sample is applied. Surrounding the platinum contact, in the base of the cell, but separated therefrom by an insulating sleeve is an annular Ag/AgCl reference electrode. The electrode cell is polarised at various potentials relative to the Ag/Ag/Cl electrode and the output current monitored at various potentials.

The invention is illustrated by the following Examples in which the electrode material is a platinised carbon paper (PCP) as supplied by the Prototech Company of Newton Highlands, Mass. and developed by them as gas diffusion electrodes. The PCP electrode material is prepared according to the teachings of U.S. Pat. No. 4,044,193 by initially platinising carbon powder particles (Vulcan XC-72), nominal particle size 30 nm) by the oxidative decomposition of a complex platinum sulfite acid in the presence of the carbon powder using $H_2O_2$, thereby to deposit colloidal platinum, particle size 1.5 to 2.5 nm, on the surface of the carbon powder particles. Following platinisation, the platinised carbon powder is subsequently moulded and bonded onto the surface of a commercial, graphitised electrically conducting carbon paper using approximately 50% by weight, based on platinised carbon powder, of polytetrafluoroethylene as the binder. The resulting platinised carbon paper electrode material has a thickness in the range 0.1 to 0.5 mm, and a platinum loading of 0.24 mg.cm$^{-2}$. For the purpose of the following tests (Examples 1 to 3), the carbon paper electrode material was cut into 5 mm diameter discs and mounted on the platinised working electrode of the cell system shown in FIG. 1 of the accompanying drawings. The actual area of the carbon paper electrode exposed to the sample in each case is approximately 0.16 cm$^2$.

The results obtained are as follows:

EXAMPLE 1

Electrochemical Oxidation of NADH on Platinised Carbon Paper (PCP)

Figure 2:
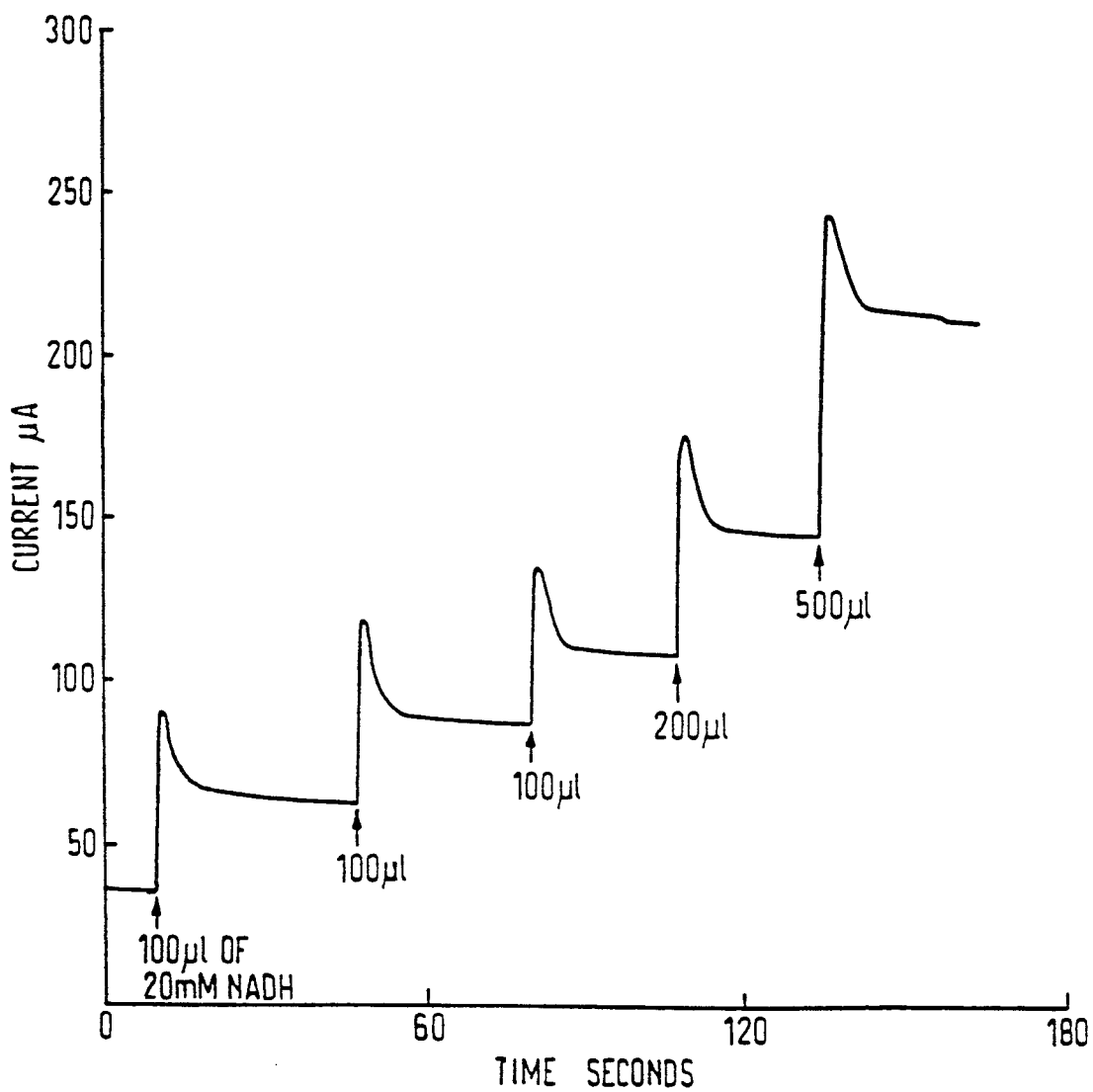
FIG. 2 shows the electrode response to successive additions of NADH to the cell using a platinised carbon paper (PCP) electrode according to this invention.
Figure 3:
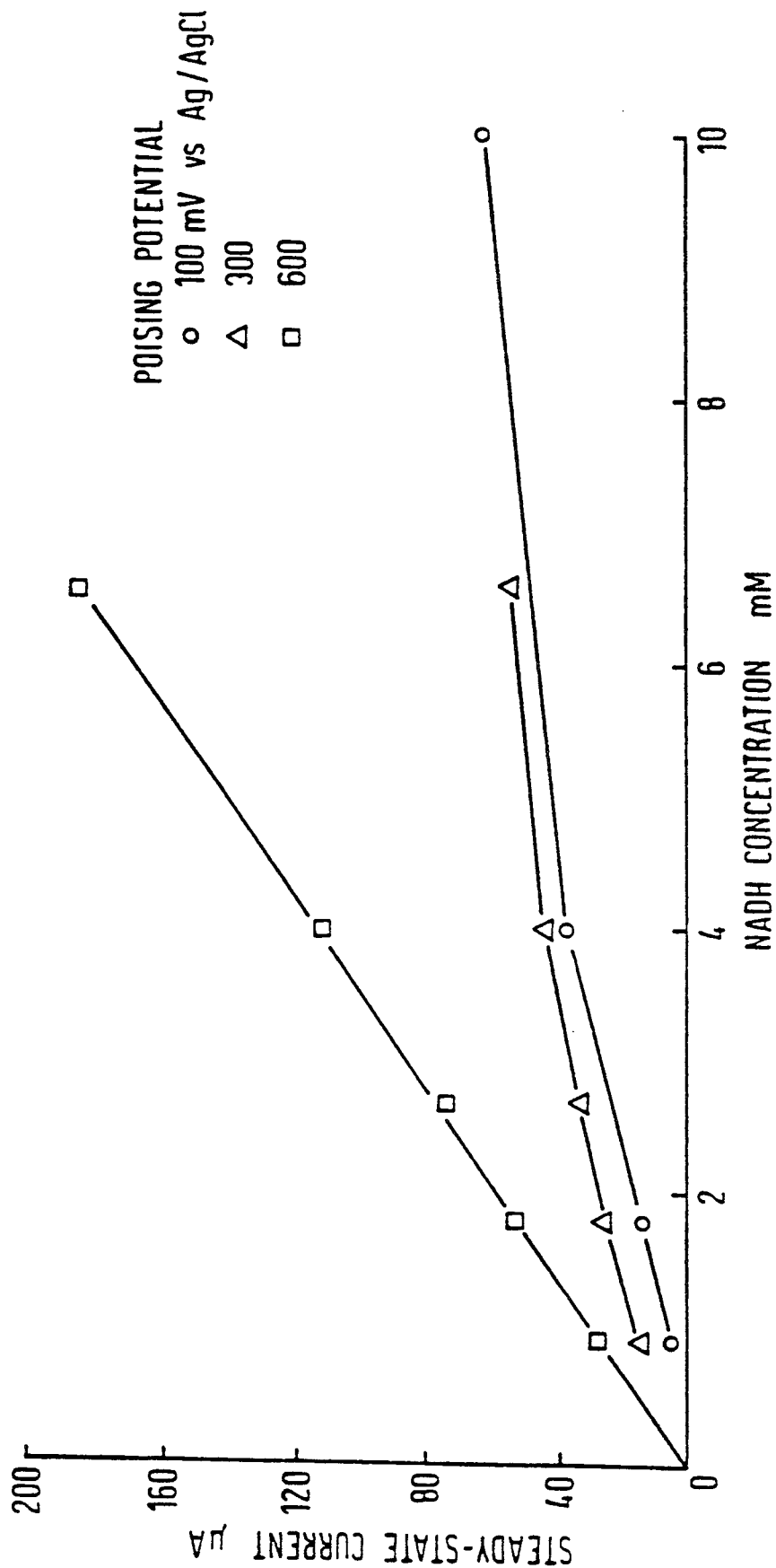
FIG. 3 shows the response of the PCP electrode to NADH at various poising potentials versus the Ag-/AgCl reference electrode.

Using a standard potentiostatic technique, samples of a 20 mM NADH solution in Tris/HCl pH 9 buffer were added to the cell containing 2 ml of 0.1M pH 7 phosphate/1M KCl buffer solution. The platinised carbon paper electrode (PCP) was poised at various potentials with respect to the Ag/Ag/Cl reference electrode. The counter electrode was platinum. Stable current plateaus were obtained (FIG. 2) which were proportional to NADH concentration (Table 1 and FIG. 3).

TABLE 1

| Current response to platinised carbon paper to NADH at various poising potentials | | | |
|---|---|---|---|
| NADH Concentration/mM | Current Output in μA at | | |
| | 100 mV | 300 mV | 600 mV |
| 0.95 | 7 | 15 | 28 |
| 1.8 | 13 | 25 | 53 |
| 2.7 | — | 32 | 73 |
| 4.0 | 38 | 42 | 113 |
| 6.6 | — | 52 | 183 |
| 10.0 | 60 | — | — |

EXAMPLE 2

Response of NADH-Electrode System to Pyruvic Acid in the Presence of Lactate Dehydrogenase (LDH)

Figure 4:
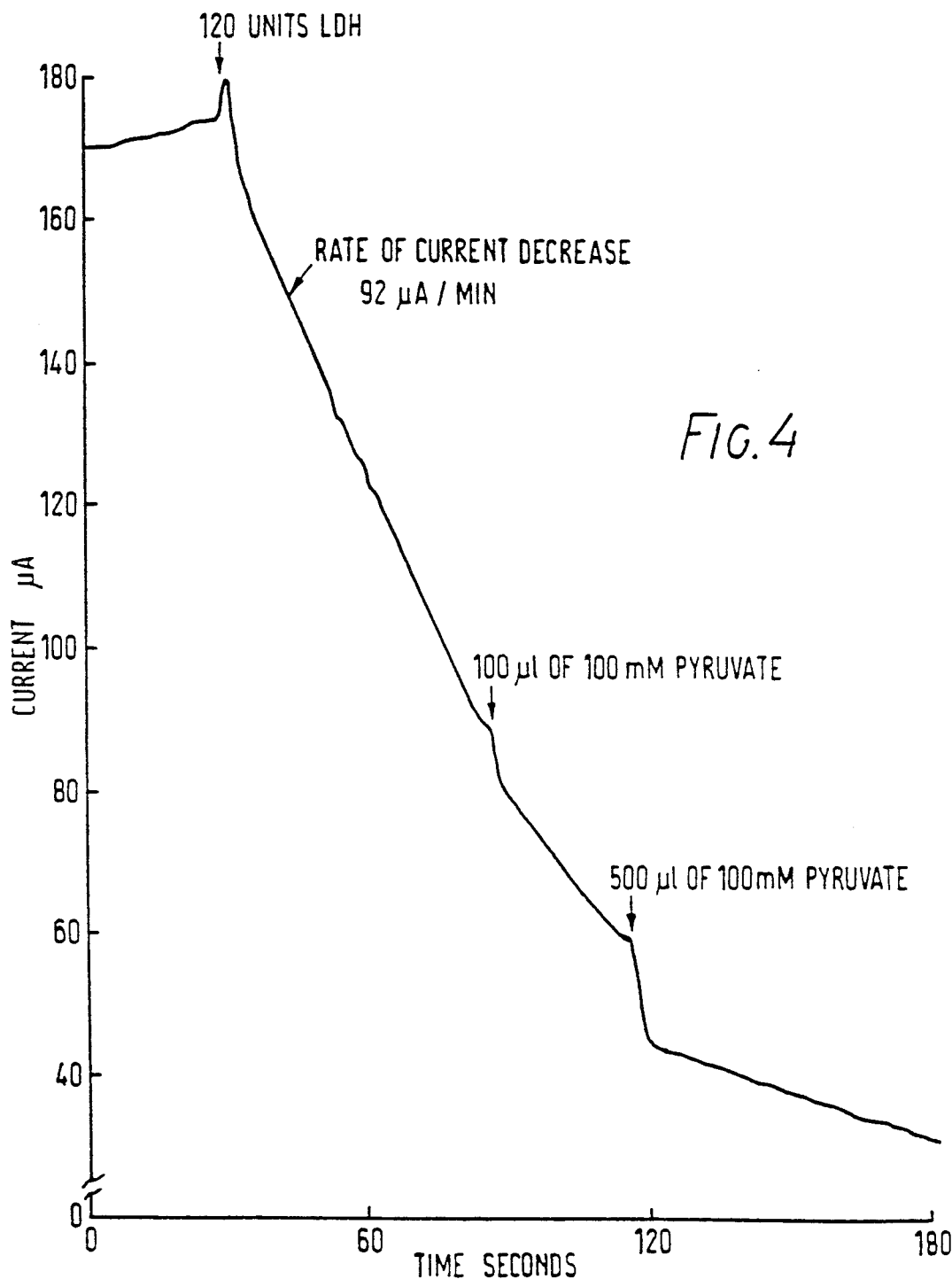
FIG. 4 shows the response of the electrode to pyruvic acid in the presence of lactate dehydrogenase (LDH)

A similar cell was set up containing 12.5 mM NADH and 10 mM pyruvic acid in 2 ml of pH 7 phosphate/KCl buffer at 25° C. The working, counter and reference electrodes were as in Example 1. The working electrode was poised at 400 mV and gave a steady signal of 170 μA above background. On addition of 120 units of LDH (bovine heart Type XV) the current decreased at an initial rate of 92 μA/min (FIG. 4) showing that the enzymatic conversion of pyruvate to lactate is efficiently monitored via the agency of NADH electrochemically coupled to the electrode.

EXAMPLE 3

Figure 5:
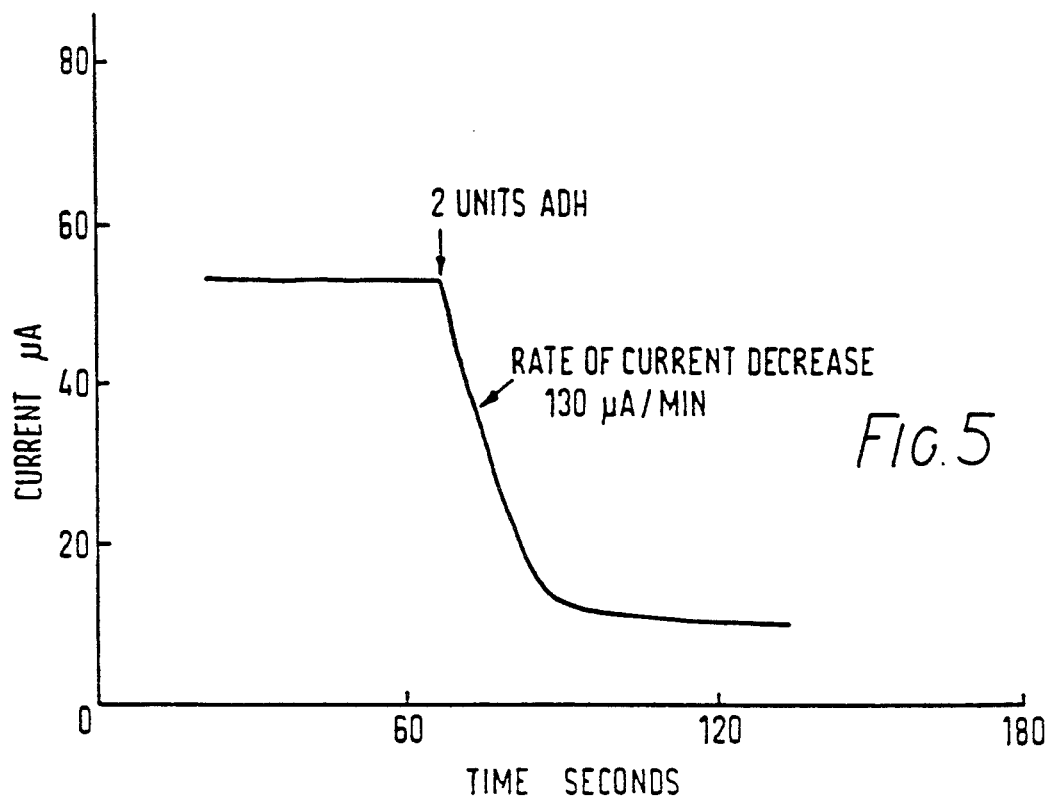
FIG. 5 shows the response of the electrode to acetaldehyde in the presence of alcohol dehydrogenase (ADH)

Response of NADH-electrode System to Acetaldehyde in the Presence of Alcohol Dehydrogenase (ADH) on a PCP Electrode The cell was set up containing 3 mM NADH and 35 mM acetaldehyde in 2 ml of pH 9 Tris/HCl buffer at 25° C. The working, counter and reference electrodes were as in Example 1. The working electrode was poised at 400 mV and gave a steady signal of 40 μA above background. On addition of 2 units of ADH (equine liver) the current decreased at an initial rate of 130 μA/min (FIG. 5) showing that the enzymatic conversion of acetaldehyde to ethanol is efficiently monitored via the agency of NADH electrochemically coupled to the electrode.

In the following examples either a two electrode cell or a three electrode cell configuration was employed. The three electrode cell was as herein described and illustrated in FIG. 1. The two electrode cell was identical in construction to that shown in FIG. 16 of EP-A-0 247 850 to which reference should be made for further details.

EXAMPLE 4 (FIG. 6)

Figure 6:
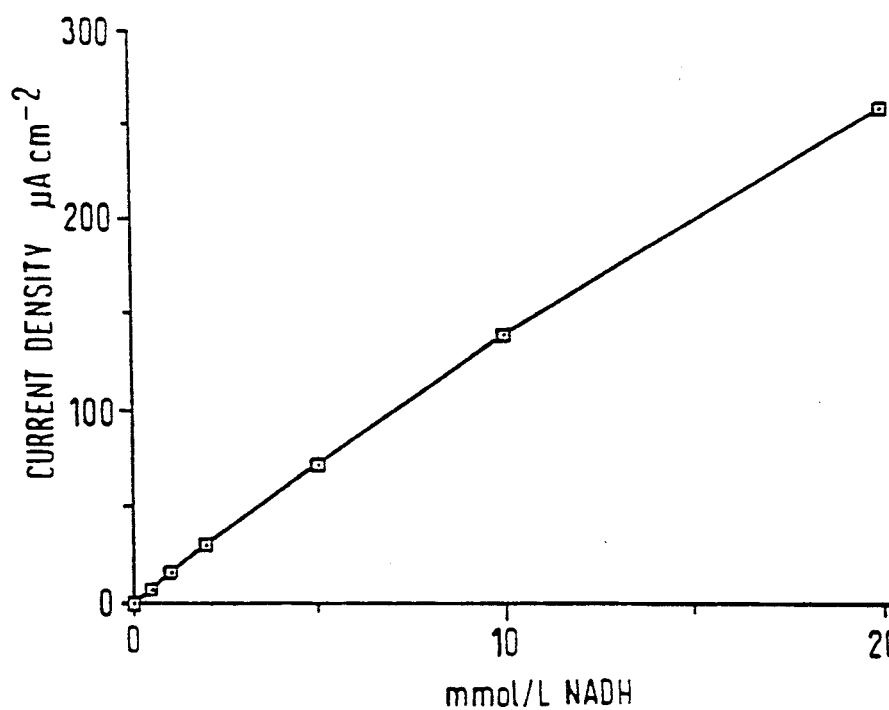
FIG. 6 is another graph showing the response of platinised carbon paper electrodes to NADH concentration in accordance with this invention.
Figure 9:
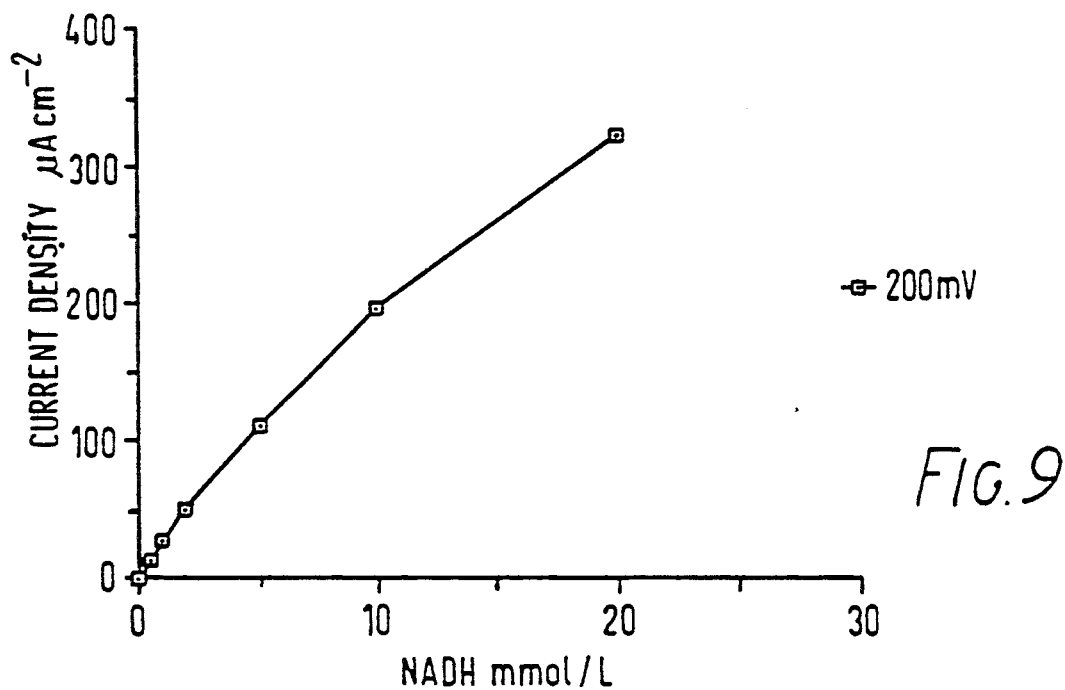
FIG. 9 shows the similar response curve for a platinum oxide containing electrode.

The data was compiled using the two electrode configuration polarised at 200 mV. A buffer of 16 mmol/L NaH$_2$PO$_4$, 53 mmol/L Na$_2$HPO$_4$, 52 mmol/L NaCl, 1.5 mmol/L ethylene diamine tetraacetic acid, pH 7.4, was used. After achieving a stable background current in this buffer, the buffer was wiped off the membrane and replaced with samples of NADH in the same buffer. The peak current was recorded. FIG. 6 shows the responses from a platinised carbon paper electrode as commercially available from the Prototech Company and comprising resin-bonded platinised carbon particles deposited on an electrically conductive carbon paper backing sheet, the resin-bonded platinised carbon layer comprising, on a weight basis, 50% polytetrafluoroethylene, 45% finely divided carbon (Vulcan XC72) and 5% colloidal platinum preadsorbed onto the carbon powder. To minimise the background current a 5 mg/ml protein solution (glucose oxidase) was adsorbed onto the electrode overnight prior to NADH measurements. It should be noted that the glucose oxidase is merely an example of a suitable protein.

EXAMPLE 5 (FIG. 7)

This illustrates the applicability of the invention to measurement of the substrates of NADH-utilizing enzymes. A three electrode cell was used as previously described but equipped with a magnetic stirrer bar. The working electrode was platinised carbon paper as in Example 4, but L-lactate dehydrogenase (EC 1.1.1.27 from beef heart) was immobilised to the electrode via carbodiimide coupling, see EP-A-0 247 850, but using a 1 mg/ml solution of lactate dehydrogenase (from Sigma Chemicals, type XV, 500 units per mg protein). The cell contained 12.5 mmol/L NADH initially, in 0.1 mol/L phosphate/1 mol/L KCl buffer, pH 7. The polarising potential was 350 mV. The apparatus could be used to monitor the consumption of NADH when aliquots pyruvic acid were added to the cell, as shown in the FIGURE.

EXAMPLE 6 (FIG. 8)

Example 5 was repeated except that the immobilised lactate dehydrogenase was replaced by glucose dehydrogenase (EC 1.1.1.47 from Bacillus spp. supplied by Sigma, 100–300 U/mg protein) immobilised onto the electrode in a similar manner. Whereas lactate dehydrogenase is used to measure pyruvic by monitoring NADH consumption

the glucose dehydrogenase is used to measure glucose by following NADH production:

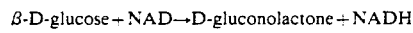

The cell contained 0.1 mol/L phosphate/0.1 mol/L KCl/2.4 mmol/L NAD, pH 7.

EXAMPLE 7 (FIG. 9)

Following the procedure outlined in Example 4, the current output of a platinum oxide containing carbon electrode is measured at 200 mV (against a Ag/AgCl reference electrode) in a two electrode cell at various NADH concentrations, and shows a substantially linear response equivalent to that of the platinised carbon paper electrodes. In this case the electrode material comprises a layer of resin-bonded (polytetrafluorethylene) carbon particles (Vulcan XC72) having 5% by weight (based on total weight of the resin-bonded particles) platinum oxide preadsorbed onto the carbon powder particles; binder 50% by weight, carbon 45% by weight, and bonded to the surface of electrically conductive Toray (trade mark) carbon paper.

EXAMPLE 8 (FIG. 10)

Figure 10:
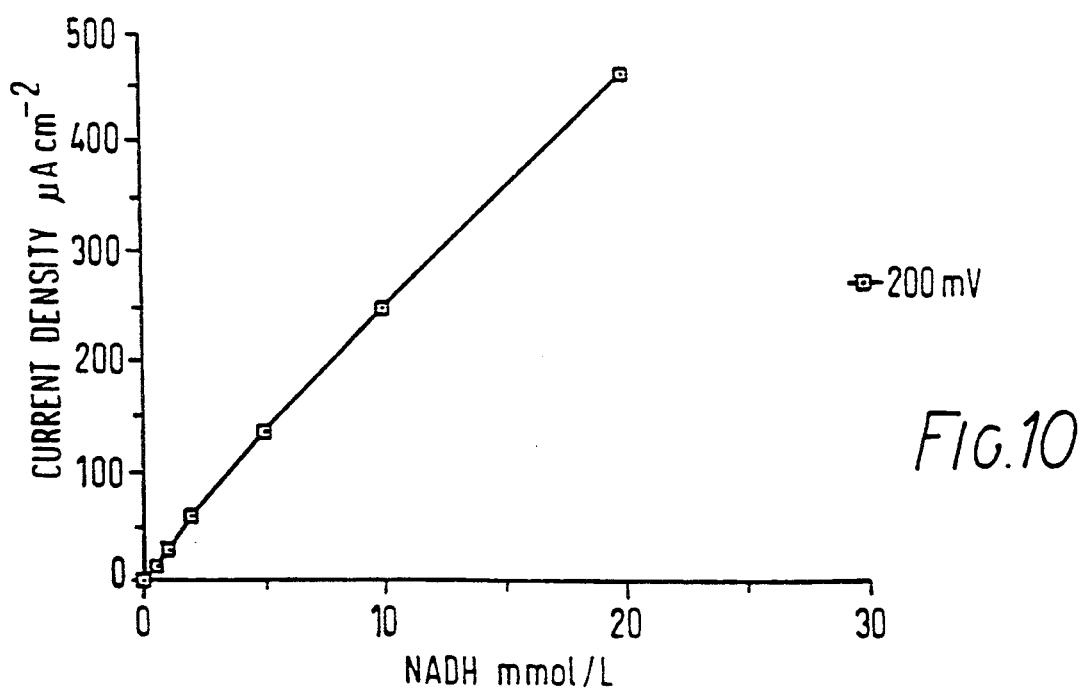
FIG. 10 shows the response curve for a palladised activated carbon electrode.

Once again, following the procedure outlined in Example 4, the current output of a palladised carbon paper electrode is measured at 200 mV (against Ag/AgCl) using the two electrode cell configuration at various NADH concentrations. Once again the response (FIG. 10) is substantially linear. The electrode material is as described in Example 7 save that the resin-bonded carbon particles comprise 5% by weight preadsorbed finely divided palladium.

The above Examples demonstrate the use of the electrode materials to produce a rapid and reproducible oxidation of NADH. These responses are in marked contrast to those given by most other electrode materials, as demonstrated in comparable experiments using platinum, glassy carbon, or graphite electrode materials, which (with rare exceptions) are generally sluggish, relatively insensitive, and of much poorer reproducibility. The effectiveness of the platinised or palladised carbon electrodes we have used appears to be a result of their particular heterogeneous structure and its compatibility with biological molecules such as NADH and enzymes. The oxidation of NADH also proceeds efficiently in the presence of enzymes and substrates, and can be used as a basis for rapid NADH-coupled enzymatic assays. The potential for efficient assay of pyruvate (using LDH) and acetaldehyde (using ADH) is clear from the above Examples, but a very large number of similar assays are also accessible using other enzymes and substrates.

Although the invention has been described herein solely with reference to the determination of NADH in solution, phosphorylated 1,4-dihydronicotinamide adenine dinucleotide (NADPH), i.e. phosphorylated NADH, may be determined by exactly the same technique. Moreover, since NADPH (or NADP) is a cofactor in a selected group of enzyme catalysed reactions, rather than NADH (or NAD), the technique of this invention enables such reactions to be monitored in exactly the same way, i.e. by amperometrically determining either the consumption or the production of NADPH in solution. Thus all references herein to NADH, or NAD, are to be taken to include the phosphorylated derivative unless the context requires otherwise.

We claim:

1. A method for the quantitative amperometric determination of NADH in solution in a liquid amenable to measurable electrochemical action of NADH therein, which comprises:

(a) contacting a sample of said liquid with an electrode, said electrode comprising in contact with the sample a porous layer of finely divided activated carbon or graphite particles having finely divided platinum or palladium adsorbed thereonto, said particles being bonded together in said layer by a resin;

(b) maintaining said electrode at a potential effective to cause oxidation of NADH in the sample; and (c) measuring the current produced.

2. A method for the quantitative amperometric determination of a compound selected from the group consisting of NADH, oxidized NADH (NAD), phosphorylated NADH (NADPH) and oxidized NADPH (NADP) in solution in a liquid amenable to measurable electrochemical action of said compound therein, which comprises:

(a) contacting a sample of said liquid with an electrode, said electrode comprising in contact with the sample a porous layer of finely divided activated carbon or graphite particles having finely divided noble metal or noble metal oxide adsorbed thereonto, said particles being bonded together in said layer by a resin;

(b) maintaining said electrode at a potential effective to cause change of the state of oxidation of said compound in the sample; and (c) measuring the current produced.

3. A method according to claim 2, wherein liquid being a clinical liquid containing NADH or NADPH.

4. A method according to claim 1 or 2, said electrode comprising an electrically conductive support member having said layer formed thereon as a surface layer of said resin-bonded particles.

5. A method according to claim 4, said support member being an electrically conductive carbon paper.

6. A method according to claim 2, said compound being NAD or NADH.

7. A method according to claim 1 or 2, said resin being a fluorocarbon resin.

8. A method according to claim 1 or 2, said resin being polytetrafluoroethylene.

9. A method according to claim 1 or 2, said activated carbon or graphite particles having particle sizes in the range of about 5 to 30 nm, and having colloidal particles of platinum or palladium adsorbed thereonto prior to being bonded together, and being bonded together by a fluorocarbon resin.

10. A method for amperometric determination of the quantity in solution in a liquid of a substance that will undergo enzymatic reaction in the liquid in the presence of an enzyme capable of catalyzing said reaction when NADH is present in the solution as a cofactor to be oxidized electrochemically concomitantly with the enzymatic reaction, which method comprises:

(a) contacting a sample of the liquid, in the presence of both said enzyme and said cofactor, with an electrode maintained at a fixed potential effective to cause oxidation of NADH in the sample, said electrode comprising in contact with the sample a porous layer of activated carbon or graphite particles having finely divided platinum or palladium adsorbed thereonto, said particles being bonded together in said layer by a resin, (b) thereby initiating the enzymatic reaction of said substance with concomitant oxidation of NADH in the sample;

(c) measuring the current produced; and (d) determining from the measured current the concentration, or change of concentration, of NADH in the sample as a result of the enzymatic reaction, whereby to determine indirectly the amount of said substance present in the sample.

11. A method for amperometric determination of the quantity in solution in a liquid of a substance that will undergo enzymatic reaction in the liquid in the presence of an enzyme capable of catalyzing said reaction when a compound selected from the group consisting of NADH, oxidized NADH (NAD), phosphorylated NADH (NADPH) and oxidized NADPH (NADP) is present in the solution as a cofactor to be reacted electrochemically concomitantly with the enzymatic reaction, which method comprises:

(a) contacting a sample of the liquid, in the presence of both said enzyme and a said cofactor, with an electrode maintained at a fixed potential effective to cause electrochemical change of the state of oxidation of said cofactor in the sample, said electrode comprising in contact with the sample a porous layer of activated carbon or graphite particles having finely divided noble metal or noble metal oxide adsorbed thereonto, said particles being bonded together in said layer by a resin, (b) thereby initiating the enzymatic reaction of said substance with concomitant change of the state of oxidation of said cofactor in the sample;

(c) measuring the current produced; and (d) determining from the measured current the concentration, or change of concentration, of cofactor in the sample as a result of the enzymatic reaction, whereby to determine indirectly the amount of said substance present in the sample.

12. A method according to claim 11, said compound being NAD or NADH.

13. A method according to claim 1, 2, 10 or 11, said electrode being a working electrode in an electrochemical cell that comprises also a counterelectrode in contact with said sample and a reference electrode relative to which the working electrode is poised at a fixed potential.

14. A method according to claim 13, said working electrode being maintained at a potential of less than 600 mV relative to said reference electrode.

15. A method according to claim 10 and 11, said enzyme being immobilized or adsorbed onto said resin-bonded particles of said layer prior to contact of the sample with said layer.

16. A method according to claim 10 or 11, said cofactor being adsorbed into said layer prior to contact of the sample with said layer so that cofactor in effective amount is supplied from the electrode into the sample when the sample is in contact with the electrode.

17. A method according to claim 15, said cofactor being adsorbed into said layer prior to contact of the sample with said layer so that at least cofactor in effective amount is supplied from the electrode into the sample when the sample is in contact with the electrode.

18. A method according to claim 10 or 11, said electrode comprising an electrically conductive support member having said layer formed thereon as a thin surface layer of said resin-bonded particles; said activated carbon or graphite particles having sizes in the range of about 5 to 30 nm, having colloidal platinum particles pre-adsorbed thereon, and being bonded together by a fluorocarbon resin.

19. A method according to claim 18, said support member being an electrically conductive carbon paper.

20. An enzyme electrode for use in amperometric determination of the quantity in a liquid sample of a substance that will undergo enzymatic reaction in the sample in the presence of an enzyme capable of catalyzing said reaction when also in the presence of NADH in solution as a cofactor to be oxidized electrochemically concomitantly with the enzymatic reaction, said electrode comprising (a) a porous layer of finely divided activated carbon or graphite particles having finely divided platinum or palladium adsorbed thereonto, said particles being bonded together in said layer by a resin;

(b) a said enzyme adsorbed or immobilized in said layer; and (c) NADH adsorbed in said layer so as to be supplied therefrom into solution in the sample, for oxidation in the sample concomitantly with the enzymatic reaction of said substance therein, when the sample is in contact with said layer and an electrical potential is applied through said electrode, whereby electrochemical change of the state of oxidation of said cofactor may be sensed via the electrode to indicate indirectly the concentration of said substance in the sample.

21. An enzyme electrode for use in the aperometric determination of the quantity in a liquid sample of a substance that will undergo enzymatic reaction in the sample in the presence of an enzyme capable of catalyzing said reaction when also in the presence in solution of a cofactor, selected from the group consisting of NADH, oxidized NADH (NAD), phosphorylated NADH (NADPH) and oxidized NADPH (NADP), to be oxidized or reduced electrochemically concomitantly with the enzymatic reaction, said enzyme electrode comprising (a) a porous layer of finely divided activated carbon or graphite particles having finely divided noble metal or noble metal oxide adsorbed thereonto, said particles being bonded together in said layer by a resin;
(b) a said enzyme adsorbed or immobilized in said layer; and
(c) a said cofactor adsorbed in said layer so as to be supplied therefrom into solution in the sample for electrochemical reaction in the sample concomitantly with the enzymatic reaction of said substance therein when the sample is in contact with said layer and an electrical potential is applied through said electrode, whereby electrochemical change of the state of oxidation of said cofactor may be sensed via the electrode to indicate indirectly the concentration of said substance in the sample.

22. An enzyme electrode according to claim 20 or 21, said electrode comprising an electrically conductive support member having said layer formed thereon as a thin surface layer of said resin-bonded particles; said activated carbon or graphite particles having sizes in the range of about 5 to 30 nm, having colloidal platinum particles adsorbed thereon, and being bonded together by a fluorocarbon resin.

23. An enzyme electrode according to claim 22, said support member being an electrically conductive carbon paper.

24. An enzyme electrode according to claim 21, said adsorbed cofactor being NAD or NADH.

* * * * *